(12) United States Patent
MacDonald et al.

(10) Patent No.: US 7,655,829 B2
(45) Date of Patent: Feb. 2, 2010

(54) ABSORBENT PAD WITH ACTIVATED CARBON INK FOR ODOR CONTROL

(75) Inventors: John Gavin MacDonald, Decatur, GA (US); Jeffrey E. Fish, Dacula, GA (US); Sharon Linda Greene, Canton, GA (US); Jaeho Kim, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 440 days.

(21) Appl. No.: 11/194,102

(22) Filed: Jul. 29, 2005

(65) Prior Publication Data

US 2007/0026209 A1    Feb. 1, 2007

(51) Int. Cl.
*A61F 13/15* (2006.01)
*A61F 13/20* (2006.01)
*A61M 1/00* (2006.01)

(52) U.S. Cl. ............... 604/359; 604/358; 604/317
(58) Field of Classification Search ............... 604/358, 604/317
See application file for complete search history.

(56) References Cited

U.S. PATENT DOCUMENTS

| | | |
|---|---|---|
| 2,593,146 A | 4/1952 | Howard |
| 2,690,415 A | 9/1954 | Shuler |
| 3,149,023 A | 9/1964 | Bodendorf et al. |
| 3,338,992 A | 8/1967 | Kinney |
| 3,340,875 A | 9/1967 | Dudley et al. |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,573,158 A | 3/1971 | Pall et al. |
| 3,692,618 A | 9/1972 | Dorschner et al. |
| 3,769,144 A | 10/1973 | Economy et al. |
| 3,802,817 A | 4/1974 | Matsuki et al. |
| 3,849,241 A | 11/1974 | Butin et al. |

(Continued)

FOREIGN PATENT DOCUMENTS

BE    815446    9/1974

(Continued)

OTHER PUBLICATIONS

Abstract of Japanese Patent No. JP62297185, Dec. 24, 1987.

(Continued)

*Primary Examiner*—Tatyana Zalukaeva
*Assistant Examiner*—Susan Su
(74) *Attorney, Agent, or Firm*—Dority & Manning, P.A.

(57) ABSTRACT

An absorbent pad configured for placement under a patient to absorb bodily fluids includes a liquid permeable cover layer, a liquid impermeable back sheet, and an absorbent structure disposed between the cover layer and the back sheet. At least one of the cover layer, back sheet, or absorbent structure incorporates a dried application of a liquid activated carbon ink having activated carbon, a binder, and a solvent, with the dried application of ink having a solids add-on level of at least about 2%. The activated carbon ink is applied in a pattern over between about 25% to about 95% of a total upper surface area of the pad and presents a visually contrasting color against a background color of the pad or a contrasting ink.

19 Claims, 3 Drawing Sheets

U.S. PATENT DOCUMENTS

| | | |
|---|---|---|
| 3,939,838 A | 2/1976 | Fujinami et al. |
| 3,960,494 A | 6/1976 | Verma et al. |
| 4,100,324 A | 7/1978 | Anderson et al. |
| 4,217,386 A | 8/1980 | Arons et al. |
| 4,235,027 A | 11/1980 | Singh |
| 4,285,343 A | 8/1981 | McNair |
| 4,289,513 A | 9/1981 | Brownhill et al. |
| RE30,797 E | 11/1981 | Davis |
| 4,323,534 A | 4/1982 | DesMarais |
| 4,340,563 A | 7/1982 | Appel et al. |
| 4,341,216 A | 7/1982 | Obenour |
| 4,375,448 A | 3/1983 | Appel et al. |
| 4,407,960 A | 10/1983 | Tratnyek |
| 4,433,024 A | 2/1984 | Eian |
| 4,459,332 A | 7/1984 | Giglia |
| 4,472,541 A | 9/1984 | Sorensen et al. |
| 4,490,145 A | 12/1984 | Campbell |
| 4,494,278 A | 1/1985 | Kroyer et al. |
| 4,511,488 A | 4/1985 | Matta |
| 4,517,308 A | 5/1985 | Ehlenz et al. |
| 4,525,410 A | 6/1985 | Hagiwara et al. |
| 4,565,727 A | 1/1986 | Giglia et al. |
| 4,608,047 A | 8/1986 | Mattingly |
| 4,640,810 A | 2/1987 | Laursen et al. |
| 4,662,005 A | 5/1987 | Grier-Idris |
| 4,663,220 A | 5/1987 | Wisneski et al. |
| 4,677,019 A | 6/1987 | Von Blucher |
| 4,680,221 A | 7/1987 | Murayama et al. |
| 4,687,478 A | 8/1987 | Van Tilburg |
| 4,715,857 A | 12/1987 | Juhasz et al. |
| 4,732,805 A | 3/1988 | Maggs |
| 4,748,065 A | 5/1988 | Tanikella |
| 4,758,239 A | 7/1988 | Yeo et al. |
| 4,762,738 A | 8/1988 | Keyes et al. |
| 4,772,455 A | 9/1988 | Izumi et al. |
| 4,775,582 A | 10/1988 | Abba et al. |
| 4,795,668 A | 1/1989 | Krueger et al. |
| 4,802,473 A | 2/1989 | Hubbard et al. |
| 4,818,464 A | 4/1989 | Lau |
| 4,833,003 A | 5/1989 | Win et al. |
| 4,834,738 A | 5/1989 | Kielpikowski et al. |
| 4,853,281 A | 8/1989 | Win et al. |
| 4,904,343 A | 2/1990 | Giglia et al. |
| 4,920,960 A | 5/1990 | Hubbard et al. |
| 4,938,753 A | 7/1990 | Van Gompel et al. |
| 4,940,464 A | 7/1990 | Van Gompel et al. |
| 4,950,264 A | 8/1990 | Osborn, III |
| 4,952,552 A | 8/1990 | Chapman et al. |
| 4,969,457 A | 11/1990 | Hubbard et al. |
| 4,978,615 A | 12/1990 | Aoyama et al. |
| 4,992,326 A | 2/1991 | Dabi |
| 5,009,653 A | 4/1991 | Osborn, III |
| 5,020,533 A | 6/1991 | Hubbard et al. |
| 5,046,604 A | 9/1991 | Forhetz et al. |
| 5,057,368 A | 10/1991 | Largman et al. |
| 5,069,970 A | 12/1991 | Largman et al. |
| 5,079,792 A | 1/1992 | D'Haen |
| 5,085,654 A | 2/1992 | Buell |
| 5,093,422 A | 3/1992 | Himes |
| 5,108,739 A | 4/1992 | Kurihara et al. |
| 5,108,820 A | 4/1992 | Kaneko et al. |
| 5,122,407 A | 6/1992 | Yeo et al. |
| 5,154,966 A | 10/1992 | Tohyama et al. |
| 5,161,686 A | 11/1992 | Weber et al. |
| 5,162,074 A | 11/1992 | Hills |
| 5,183,656 A | 2/1993 | Uesaka et al. |
| 5,190,563 A | 3/1993 | Herron et al. |
| 5,197,959 A | 3/1993 | Buell |
| 5,209,998 A | 5/1993 | Kavassalis et al. |
| 5,221,573 A | 6/1993 | Baigas, Jr. |
| 5,230,958 A | 7/1993 | Dabi |
| 5,267,992 A | 12/1993 | Van Tilburg |
| 5,272,236 A | 12/1993 | Lai et al. |
| 5,277,976 A | 1/1994 | Hogle et al. |
| 5,278,272 A | 1/1994 | Lai et al. |
| 5,281,437 A | 1/1994 | Singh |
| 5,284,703 A | 2/1994 | Everhart et al. |
| 5,304,599 A | 4/1994 | Himes |
| 5,306,487 A | 4/1994 | Karapasha et al. |
| D347,090 S | 5/1994 | Brunson |
| 5,308,346 A | 5/1994 | Sneller et al. |
| D347,713 S | 6/1994 | Brunson |
| 5,322,061 A | 6/1994 | Brunson |
| 5,332,613 A | 7/1994 | Taylor et al. |
| 5,336,552 A | 8/1994 | Strack et al. |
| 5,342,333 A | 8/1994 | Tanzer et al. |
| 5,342,342 A | 8/1994 | Kitaoka |
| 5,350,624 A | 9/1994 | Georger et al. |
| 5,364,380 A | 11/1994 | Tanzer et al. |
| 5,382,400 A | 1/1995 | Pike et al. |
| 5,383,450 A | 1/1995 | Hubbard et al. |
| 5,407,442 A | 4/1995 | Karapasha |
| 5,429,628 A | 7/1995 | Trinh et al. |
| 5,466,410 A | 11/1995 | Hills |
| 5,486,410 A | 1/1996 | Groeger et al. |
| 5,503,076 A * | 4/1996 | Yeo .................. 101/483 |
| 5,509,914 A | 4/1996 | Osborn, III |
| 5,527,171 A | 6/1996 | Soerensen |
| 5,539,056 A | 7/1996 | Yang et al. |
| 5,540,916 A | 7/1996 | Parks |
| H001579 H * | 8/1996 | Furio .................. 502/402 |
| 5,553,608 A | 9/1996 | Reese et al. |
| 5,569,234 A | 10/1996 | Buell et al. |
| 5,578,255 A | 11/1996 | Okuyama et al. |
| 5,595,828 A | 1/1997 | Weber et al. |
| 5,596,052 A | 1/1997 | Resconi et al. |
| 5,628,737 A | 5/1997 | Dobrin et al. |
| 5,634,916 A | 6/1997 | Lavon et al. |
| 5,649,916 A | 7/1997 | DiPalma et al. |
| 5,678,247 A | 10/1997 | Vickers |
| 5,681,380 A | 10/1997 | Nohr et al. |
| 5,693,385 A | 12/1997 | Parks |
| 5,702,378 A | 12/1997 | Widlund et al. |
| 5,706,535 A | 1/1998 | Takashima |
| 5,714,445 A | 2/1998 | Trinh et al. |
| 5,716,349 A | 2/1998 | Taylor et al. |
| 5,724,964 A | 3/1998 | Brunson et al. |
| 5,733,272 A | 3/1998 | Brunner et al. |
| 5,769,832 A | 6/1998 | Hasse |
| 5,780,020 A | 7/1998 | Peterson et al. |
| 5,813,398 A | 9/1998 | Baird et al. |
| 5,834,114 A | 11/1998 | Economy et al. |
| 5,836,932 A | 11/1998 | Buell et al. |
| 5,843,057 A | 12/1998 | McCormack |
| 5,846,696 A | 12/1998 | Ram et al. |
| 5,855,999 A | 1/1999 | McCormack |
| 5,860,391 A | 1/1999 | Maxwell et al. |
| 5,861,144 A | 1/1999 | Peterson et al. |
| 5,874,067 A | 2/1999 | Lucas et al. |
| 5,883,028 A | 3/1999 | Morman et al. |
| 5,932,495 A | 8/1999 | Boney et al. |
| 5,932,497 A | 8/1999 | Morman et al. |
| 5,948,398 A | 9/1999 | Hanamoto et al. |
| 5,997,981 A | 12/1999 | McCormack et al. |
| 6,002,064 A | 12/1999 | Kobylivker et al. |
| 6,015,764 A | 1/2000 | McCormack et al. |
| 6,037,281 A | 3/2000 | Mathis et al. |
| 6,096,299 A | 8/2000 | Guarracino et al. |
| 6,110,158 A | 8/2000 | Kielpikowski |
| 6,111,163 A | 8/2000 | McCormack et al. |
| 6,114,024 A | 9/2000 | Forte |
| 6,153,209 A | 11/2000 | Vega et al. |
| 6,173,712 B1 | 1/2001 | Brunson |
| 6,198,018 B1 | 3/2001 | Curro |

| | | |
|---|---|---|
| 6,200,669 B1 | 3/2001 | Marmon et al. |
| 6,203,810 B1 | 3/2001 | Alemany et al. |
| 6,231,719 B1 | 5/2001 | Garvey et al. |
| 6,245,693 B1 | 6/2001 | Gagliardi et al. |
| 6,254,401 B1 | 7/2001 | Lee |
| 6,344,218 B1 | 2/2002 | Dodd et al. |
| 6,358,537 B1 | 3/2002 | Hoshino et al. |
| 6,380,455 B1 | 4/2002 | Moder et al. |
| 6,391,429 B1 | 5/2002 | Senkus et al. |
| 6,417,424 B1 | 7/2002 | Bewick-Sonntag et al. |
| 6,427,693 B1 | 8/2002 | Blackstock et al. |
| 6,436,128 B1 | 8/2002 | Usui |
| 6,460,989 B1 | 10/2002 | Yano et al. |
| 6,461,457 B1 | 10/2002 | Taylor et al. |
| 6,467,897 B1 | 10/2002 | Wu et al. |
| 6,475,601 B1 | 11/2002 | Sakaki et al. |
| 6,479,150 B1 | 11/2002 | Liu et al. |
| 6,517,199 B1 | 2/2003 | Tomioka et al. |
| 6,517,906 B1 | 2/2003 | Economy et al. |
| 6,521,553 B1 | 2/2003 | Tabata et al. |
| 6,524,379 B2 | 2/2003 | Norh et al. |
| 6,536,890 B1 | 3/2003 | Kato et al. |
| 6,573,212 B2 | 6/2003 | McCrae et al. |
| 6,603,054 B2 | 8/2003 | Chen et al. |
| 6,617,490 B1 | 9/2003 | Chen et al. |
| 6,639,004 B2 | 10/2003 | Falat et al. |
| 6,645,271 B2 | 11/2003 | Seguin et al. |
| 6,649,805 B1 | 11/2003 | Carlucci et al. |
| 6,652,845 B2 | 11/2003 | Hu et al. |
| 6,657,098 B1 | 12/2003 | Niki et al. |
| 6,663,611 B2 | 12/2003 | Blaney et al. |
| 6,676,954 B2 | 1/2004 | Dai et al. |
| 6,680,289 B1 | 1/2004 | Woo et al. |
| 6,713,414 B1 | 3/2004 | Pomplun et al. |
| 6,716,203 B2 | 4/2004 | Sorebo et al. |
| 6,723,428 B1 | 4/2004 | Foss et al. |
| 6,740,406 B2 | 5/2004 | Hu et al. |
| 6,794,024 B1 | 9/2004 | Walton et al. |
| 6,972,010 B2 * | 12/2005 | Pesce et al. .............. 604/289 |
| 7,163,529 B2 * | 1/2007 | Mocadlo ............... 604/385.04 |
| 2002/0022813 A1 | 2/2002 | Bewick-Sonntag et al. |
| 2002/0149656 A1 | 10/2002 | Nohr et al. |
| 2003/0022787 A1 | 1/2003 | McCrae et al. |
| 2003/0113289 A1 | 6/2003 | Hu et al. |
| 2003/0114809 A1 | 6/2003 | Gagliardi et al. |
| 2003/0116462 A1 | 6/2003 | Sorebo et al. |
| 2004/0043688 A1 | 3/2004 | Soerens et al. |
| 2004/0044319 A1 * | 3/2004 | Bewick-Sonntag et al. .. 604/360 |
| 2004/0116882 A1 * | 6/2004 | Erspamer et al. ............ 604/359 |
| 2004/0121681 A1 | 6/2004 | Lindsay et al. |
| 2004/0121688 A1 | 6/2004 | Edens et al. |
| 2004/0122386 A1 * | 6/2004 | Mocadlo ..................... 604/359 |
| 2004/0122387 A1 | 6/2004 | Long et al. |
| 2004/0122399 A1 | 6/2004 | McDaniel |
| 2004/0166248 A1 | 8/2004 | Hu et al. |
| 2004/0176736 A1 | 9/2004 | Christon et al. |
| 2005/0098466 A1 | 5/2005 | Thomas |
| 2006/0111684 A1 * | 5/2006 | Berba et al. ................. 604/361 |

FOREIGN PATENT DOCUMENTS

| | | |
|---|---|---|
| DE | 196 03840 A1 | 1/1997 |
| DE | 198 16393 A1 | 1/1999 |
| EP | 0282287 B2 | 9/1988 |
| EP | 0348978 A2 | 1/1990 |
| EP | 0 389 023 A2 | 9/1990 |
| EP | 0392528 A2 | 10/1990 |
| EP | 0510619 A1 | 10/1992 |
| EP | 0515503 B1 | 10/1995 |
| EP | 0749295 B1 | 12/1996 |
| EP | 0811390 B1 | 12/1997 |
| EP | 0955087 A1 | 11/1999 |
| EP | 1034800 A1 | 9/2000 |
| EP | 0850617 B1 | 10/2001 |
| EP | 0839462 B1 | 12/2001 |
| EP | 1188854 A1 | 3/2002 |
| EP | 0691856 B1 | 6/2002 |
| EP | 0835089 B1 | 9/2002 |
| EP | 0811392 B1 | 10/2002 |
| EP | 1180995 B1 | 11/2003 |
| GB | 1549012 | 7/1979 |
| WO | WO 8604367 | 7/1986 |
| WO | WO 9112029 A1 | 8/1991 |
| WO | WO 9112030 A1 | 8/1991 |
| WO | WO 9820915 A1 | 5/1998 |
| WO | WO 9826808 A2 | 6/1998 |
| WO | WO 9826808 A3 | 6/1998 |
| WO | WO 9900093 A1 | 1/1999 |
| WO | WO 9912734 A1 | 3/1999 |
| WO | WO 02055115 A1 | 7/2002 |
| WO | WO 02101140 | 12/2002 |
| WO | WO 03000979 A2 | 1/2003 |
| WO | WO 03051414 | 6/2003 |
| WO | WO 03089019 | 10/2003 |
| WO | WO 2004011044 | 2/2004 |
| WO | 2004 060421 A | 7/2004 |
| WO | 2006 071313 A | 7/2006 |
| WO | 2006 071318 A | 7/2006 |

OTHER PUBLICATIONS

Abstract of Japanese Patent No. JP813352, Feb. 14, 1996.
Abstract of Japanese Patent No. JP03195562, Aug. 27, 1991.
Abstract of Japanese Patent No. JP03221142, Sep. 30, 1991.
Abstract of Japanese Patent No. JP06285140, Oct. 11, 1994.
Article—*Adsorption of Dyes on Nanosize Modified Silica Particles*, Guangwei Wu, Athanasia Koliadima, Yie-Shein Her, and Egon Matijevic, Journal of Colloid and Interface Science, vol. 195, 1997, pp. 222-228.
Article—*Adsorption Of Gases In Multimolecular Layers*, Stephen Brunauer, P. H. Emmett, and Edward Teller, The Journal of the American Chemical Society, vol. 60, Feb. 1938, pp. 309-319.
Pocket Guide to Digital Printing, Frank Cost, Delmar Publishers, Albany, NY, ISBN 0-8273-7592-1, pp. 144-145.
ASTM Designation: D737-96, "Standard Test Method for Air Permeability of Textile Fabrics", Published Apr. 1996, pp. 207-211.
ASTM Designation: E 1207-87, "Standard Practice for The Sensory Evaluation of Axillary Deodorancy", Published Feb. 1988, pp. 51-66.
Ball, K., "The Hazards of Surgical Smoke", *ANNA Journal*, Apr. 2001, vol. 69, No. 2, pp. 125-132.
Lowe, C. et al., *Chemistry & Technology for UV & EB Formulation for Coatings, Inks, & Paints*, vol. 4, Formulation, 1997, John Wiley & Sons, SITA Technology, Ltd., ISBN 0 947798 54 4, 2 pages.
Product Data Bulletin on Nuchar® SA-20 from MeadWestvaco Corporation, 2002, 1 page.
Product Data Bulletin on Nuchar® SA-1500 from MeadWestvaco Corporation, 2002, 1 page.
PCT Search Report, May 31, 2007.

* cited by examiner

ABSORBENT PAD WITH ACTIVATED CARBON INK FOR ODOR CONTROL

BACKGROUND OF THE INVENTION

Absorbent bed pads or "under pads" are widely used in the medical and health care fields. These pads are generally placed under patients confined to a bed or chair, or during certain types of medical procedures, to absorb bodily fluids while also protecting the bed or chair. Such pads play an important role in patient care in that they rapidly absorb fluids that could cause complications if the patient were to remain in contact with the fluids over a prolonged time. The pads also protect bed linens and thus reduce bed changes and washings. Many of the fluids absorbed by the bed pads, however, result in generation of significant malodorous compounds, particularly during degradation of the substances.

Although it is well known to incorporate various odor control additives into personal hygiene absorbent articles, development of effective odor control for bed pads has lagged. One reason for this may be the cost and processes for applying conventional odor control substances in an amount needed for effective odor control in relatively large bed pads. For instance, activated carbon is widely used to reduce a broad spectrum of odors but, in spite of its excellent properties as an adsorbent, the use of activated carbon in disposable absorbent articles has been limited by its black color. Many consumers associate the traditionally black color of activated carbon with a dirty or grimy material. This condition would only be emphasized in large bed pads wherein the activated carbon would be spread over a large surface area.

U.S. Pat. No. 5,706,535 describes one attempt to provide odor control for bedding articles wherein pockets containing deodorizer elements are configured with the articles. This configuration would not be particularly useful for bed pads.

As such, a need currently exists for bed pads having improved odor control capabilities.

SUMMARY OF THE INVENTION

Objects and advantages of the invention will be set forth in part in the following description, or may be obvious from the description, or may be learned through practice of the invention.

The present invention relates to an absorbent odor control pad that has uses in various environments and industries, including medical, industrial, food service, printing, manufacturing, etc. It should be appreciated that the pad according to the invention is not limited to its intended use. The pad has particular usefulness in the medical arts as an absorbent bed pad, but is not limited to such use. The pad may be used in any application wherein it is desired to absorb fluids and control odor caused by the fluids. For ease of explanation only, the invention will be described and illustrated herein as a bed pad embodiment.

Thus, an absorbent pad is provided that is particularly suited for placement under a patient to absorb bodily fluids. Such pads are typically used in hospitals or health care facilities to be placed under patients confined to a bed, chair, or other support. The pads are also used during various surgical procedures to absorb bodily or other fluids. It should be appreciated that the end use of the pads is not a limiting feature of the invention.

The pads include a liquid permeable cover layer, a liquid impermeable back sheet, and an absorbent structure disposed between the cover layer and the back sheet. Various materials well suited for these components are well know in the art of absorbent articles, and the invention is not limited to any one or combination of materials.

At least one of the cover layer, back sheet, or absorbent structure incorporates a dried application of an activated carbon ink, the ink having been applied in liquid form and including activated carbon, a binder, and a solvent. The dried application of the ink has a solids add-on level of at least about 2%, and the ink is applied in a pattern over between about 12% to about 95% of a total exposed upper surface area of the pad. The ink is applied in any desired aesthetically pleasing pattern that presents a visually contrasting color against a background color of the pad. For example, the ink may be applied in stripes, floral design, geometric patterns, abstract patterns, and so forth.

In a particular application of the ink, the activated carbon comprises from about 1 wt. % to about 50 wt. % of the liquid ink. The binder may comprise from about 0.01 to about 30 wt. % of the liquid ink. The solvent may comprise from about 40 wt. % to about 99 wt. % of the liquid ink.

In a particular embodiment, the pattern of dried activated carbon ink desirably covers from about 30% to about 90% of the exposed upper surface area of the pad and the contrast between the color of the dried activated carbon ink and the background color has a minimum gray scale value of at least about 45 on a scale of 0-255.

The pad may also include a dried application of an additional ink on at least one of the cover layer, back sheet, or the absorbent structure that presents a color that is visually distinguishable from the color of the activated carbon ink. This additional ink may or may not include activated carbon. In a particular embodiment, the activated carbon ink and additional ink are applied in an overlapping relationship, or a non-overlapping relationship.

The activated carbon ink may be applied to any combination of the pad components. For example, each of the layers of the pad may have a portion of the overall application of the ink such that each layer contributes to the overall surface area coverage of the ink. For example, the cover layer may have a pattern of ink stripes that encompasses about 25% of the overall exposed surface area of the pad. The underlying absorbent structure, or an intermediate structure such as a surge layer or other type of fluid distribution material, may have an offset or overlapping pattern relative to the pattern on the cover layer that encompasses an additional 25% of the surface area. Alternatively, the activated carbon ink may be applied to only one of the pad components.

The activated carbon ink may be applied at various add-on levels depending on the anticipated malodorous compounds. For particular applications, the add-on level is between about 3 to about 10 gsm, or between about 3 to about 6 gsm.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
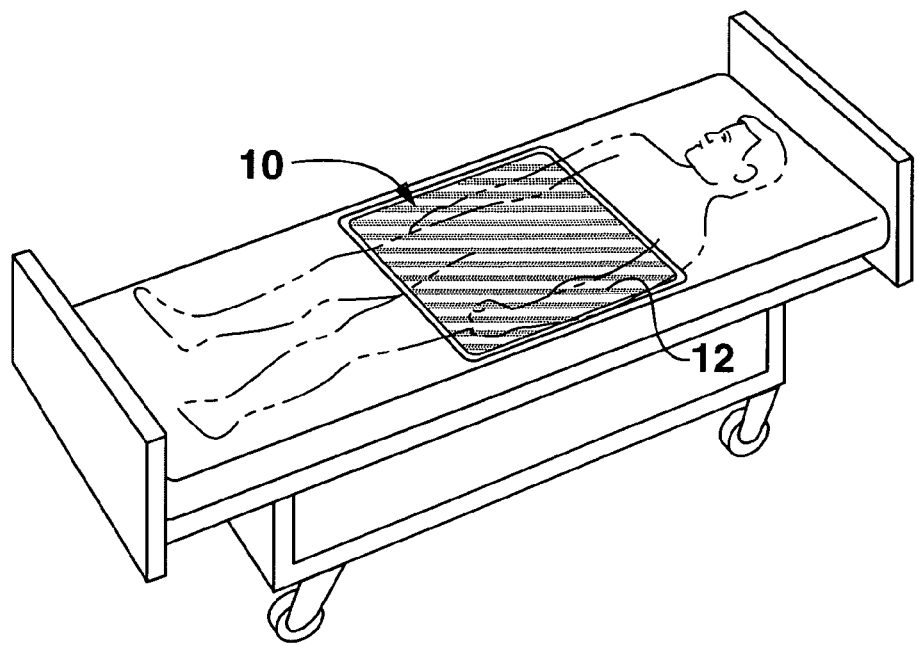
FIG. 1 illustrates an absorbent pad in accordance with the invention placed under a patient confined to a bed.

Repeat use of reference characters in the present specification and drawings is intended to represent same or analogous features or elements of the invention.

DETAILED DESCRIPTION OF REPRESENTATIVE EMBODIMENTS

Definitions

As used herein the term "nonwoven fabric or web" refers to a web having a structure of individual fibers or threads which are interlaid, but not in an identifiable manner as in a knitted fabric. Nonwoven fabrics or webs have been formed from many processes such as, for example, meltblowing processes, spunbonding processes, bonded carded web processes, etc.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. NO. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 30 microns.

As used herein, the term "breathable" means pervious to water vapor and gases. For instance, "breathable barriers" and "breathable films" allow water vapor to pass therethrough, but are substantially impervious to liquid water. The "breathability" of a material is measured in terms of water vapor transmission rate (WVTR), with higher values representing a more vapor-pervious material and lower values representing a less vapor-pervious material. Typically, the "breathable" materials have a water vapor transmission rate (WVTR) of from about 500 to about 20,000 grams per square meter per 24 hours (g/m$^2$/24 hours), in some embodiments from about 1,000 to about 15,000 g/m$^2$/24 hours, and in some embodiments, from about 1,500 to about 14,000 g/m$^2$/24 hours.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Figure 2:
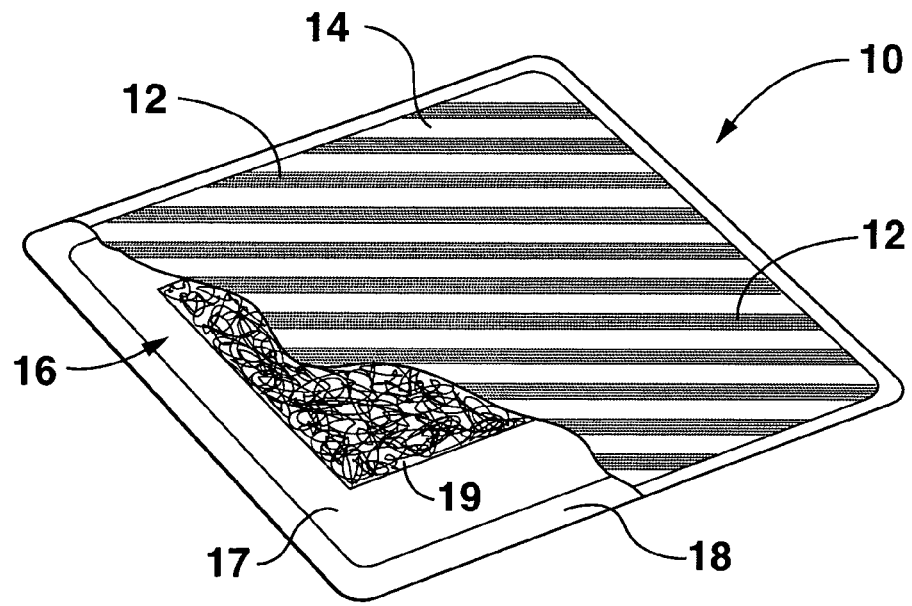
FIG. 2 is a perspective partial cut-away view of a particular embodiment of an absorbent bed pad according to the invention wherein a pattern of activated carbon ink is applied to the cover layer of the pad.

Referring to the figures in general, the present invention is directed to an absorbent pad in general. As mentioned, the pad is not limited by its intended use or point of application. For purposes of explanation only, the pad is illustrated and described herein as an "under pad" or bed pad 10 that is intended to be placed under a patient in various situations to absorb bodily fluids, as depicted in FIG. 1. The pad incorporates an application of dried activated carbon ink 12 for odor control purposes, and is not limited to any particular construction of bed pad or combination of materials. In general, such pads incorporate a liquid permeable cover layer 14, an absorbent structure 16, and a liquid impermeable back sheet or baffle 18, as depicted in FIG. 2. Exemplary non-limiting materials are described below.

The pads 10 may be disposable items, and serve a useful benefit in the disposal process in that they continue to control odors not just from the fluids absorbed by the pad, but also from malodorous compounds present in other items in the disposal container.

The pads 10 may be made in various sizes depending on their intended use, and larger sized pads may be foldable. Desirably, the application of carbon ink is applied in an amount and pattern so as not to degrade flexibility of the pad to such an extent that the pad cannot be folded.

The pad 10 is desirably provided with sufficient capacity to absorb and retain the intended amount and type of bodily exudate(s) or fluids. The absorbent capacity is provided by the fluid retentive absorbent structure 16 that can be any structure or combination of components which are generally compressible, conformable, non-irritating to a wearer's skin, and capable of absorbing and retaining liquids and certain body wastes. For example, the structure 16 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, as well as combinations thereof. In a particular embodiment, the absorbent web material is a matrix of cellulosic fluff, and may also include superabsorbent hydrogel-forming particles. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft-wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

The absorbent structure 16 can contain superabsorbent materials that are effective in retaining body fluids. As a general rule, the superabsorbent material is present in the absorbent web in an amount of from about 0 to about 90 weight percent based on total weight of the web. Superabsorbents have the ability to absorb a large amount of fluid in relation to their own weight. Typical superabsorbents used in absorbent articles, such as sanitary napkins, can absorb anywhere from 5 to 60 times their weight in body fluids. Superabsorbent materials are well known in the art and can be selected from natural, synthetic, and modified natural polymers and materials.

The absorbent structure 16 may include a coform material. The term "coform material" generally refers to composite materials comprising a mixture or stabilized matrix of thermoplastic fibers and a second non-thermoplastic material. Some examples of such coform materials are disclosed in U.S. Pat. No.4,100,324 to Anderson, et al.; U.S. Pat. No. 5,284,703 to Everhart. et al.; and U.S. Pat. No. 5,350,624 to Georger. et al.; which are incorporated herein in their entirety by reference thereto for all purposes.

The absorbent structure 16 may be a multi-layer component and may include, for example, an intake or surge layer, or other type of transfer layer in combination with the underlying absorbent web. Such combinations of materials are well known to those skilled in the art.

The fluid-permeable cover layer 14 has an outwardly facing surface that may contact the body of the wearer and receive bodily exudate(s) or fluids. The top cover 14 desirably is made of a material that is flexible and non-irritating to the wearer. As used herein, the term "flexible" is intended to refer to materials that are compliant and readily conform to the bodily surface(s) with which such materials are in contact, or materials which respond by easily deforming in the presence of external forces. The top cover 14 is provided for comfort and conformability and functions to direct bodily exudate(s) and fluids away from the body, through the top cover 14, and toward the absorbent structure 16. The top cover 14 should retain little or no liquid in its structure so that the cover provides a relatively comfortable and non-irritating surface next to patient's skin. The top cover 14 can be constructed of any woven or nonwoven material that is easily penetrated by bodily fluids that contact the surface of the cover. Examples of suitable cover materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. The cover may be apertured to increase its fluid transfer capacity. A specific example of a suitable cover material is a bonded carded web made of polypropylene and polyethylene such as that used as cover stock for KOTEX.®. pantiliners and obtainable from Sandler Corporation, Germany. Other examples of suitable materials are composite materials of polymer and nonwoven fabric materials. The composite materials are typically in the form of integral sheets generally formed by the extrusion of a polymer onto a web of spun-bonded material. The fluid permeable cover 14 can also contain a plurality of apertures formed therein which are intended to increase the rate at which bodily fluid(s) can penetrate through the cover and into the absorbent structure 16.

The top cover 14 can be maintained in secured relation with the absorbent structure 16 by bonding all or a portion of the adjacent surfaces to one another. A variety of bonding methods known to one of skill in the art can be utilized to achieve any such secured relationship. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The back sheet or baffle 18 may be any one of a number of suitable liquid impermeable materials known in the art for use as outer covers or baffles in absorbent articles. Preferably, the baffle 18 will permit the passage of air and moisture vapor out of the pad 10 while blocking the passage of body fluids. A suitable material is a micro-embossed polymeric film, such as polyethylene or polypropylene, having a thickness of about 0.025 to 0.13 millimeters. Bicomponent films can also be used, as well as woven and nonwoven fabrics which have been treated to render them liquid impermeable. A specific example of a baffle material is a polyethylene film such as that used in KOTEX.®. pantiliners and obtainable from Pliant Corporation, Schaumburg, Ill., USA. The cover can be maintained in secured relation with the absorbent structure 16 by bonding all or a portion of the adjacent surfaces to one another. A variety of bonding methods known to one of skill in the art can be utilized to achieve any such secured relation. Examples of such methods include, but are not limited to, ultrasonic bonding, thermal bonding, or the application of adhesive materials in a variety of patterns between the two adjoining surfaces.

At least one of the component substrates of the pad 10 incorporates a dried application of an activated carbon ink 12 for reducing odor. When applied in accordance with the present invention, the ink is also durable and present in an aesthetically pleasing pattern on the selected substrate. Generally speaking, activated carbon may be derived from a variety of sources, such as from sawdust, wood, charcoal, peat, lignite, bituminous coal, coconut shells, etc. Some suitable forms of activated carbon and techniques for formation thereof are described in U.S. Pat. No. 5,693,385 to Parks; U.S. Pat. No. 5,834,114 to Economy, et al.; U.S. Pat. No. 6,517, 906 to Economy, et al.; U.S. Pat. No. 6,573,212 to McCrae, et al., as well as U.S. Patent Application Publication Nos. 2002/ 0141961 to Falat, et al. and 2004/0166248 to Hu, et al., all of which are incorporated herein in their entirety by reference thereto for all purposes. The concentration of activated carbon in the ink (prior to drying) is generally tailored to facilitate odor control without adversely affecting other properties of the substrate, such as flexibility, absorbency, etc. For instance, activated carbon is typically present in the ink in an amount from about 1 wt. % to about 50 wt. %, in some embodiments from about 5 wt. % to about 25 wt. %, and in some embodiments, from about 10 wt. % to about 20 wt. %.

The activated carbon ink also generally contains a binder for increasing the durability of the activated carbon when applied to the substrate, even when present at high levels. The binder may also serve as an adhesive for bonding one substrate to another substrate. Generally speaking, any of a variety of binders may be used in the activated carbon ink of the present invention. Suitable binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the binder. The polymer suitable for use in the lattices typically has a glass transition temperature of about 30° C. or less so that the flexibility of the resulting substrate is not substantially restricted. Moreover, the polymer also typically has a glass transition temperature of about −25+ C. or more to minimize the tackiness of the polymer latex. For instance, in some embodiments, the polymer has a glass transition temperature from about −15° C. to about 15° C., and in some embodiments, from about −10° C. to about 0° C. For instance, some suitable polymer lattices that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer lattices described above may be readily varied, as is well known in the art, by utilizing a stabilizing agent having the desired charge during preparation of the polymer latex. For instance, specific techniques for an activated carbon/polymer latex system are described in more detail in U.S. Pat. No. 6,573,212 to McCrae, et al. Activated carbon/polymer latex systems that may be used in the present invention include Nuchar® PMA, DPX-8433-68A, and DPX-8433-68B, all of which are made by MeadWestvaco Corp. of Covington, Va.

Although polymer lattices may be effectively used as binders in the present invention, such compounds sometimes result in a reduction in drapability and an increase in residual odor. Thus, water-soluble organic polymers may also be employed as binders to alleviate such concerns. Another benefit of the water-soluble binder of the present invention is that it may facilitate the controlled release of the activated carbon ink from the substrate in an aqueous environment. Specifically, upon contacting an aqueous solution, the water-soluble binder dissolves and loses some of its binding qualities, thereby allowing other components of the activated carbon ink to be released from the substrate. This may be useful in various applications, such as for hard-surface wipers in which it is desired for the activated carbon ink to be released into the wiped environment for sustained odor control.

One class of water-soluble organic polymers found to be suitable in the present invention is polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Suitable cellulosic ethers may include, for instance, those available from Akzo Nobel of Covington, Va. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is ethyl hydroxyethyl cellulose having a degree of ethyl substitution (DS) of 0.8 to 1.3 and a molar substitution (MS) of hydroxyethyl of 1.9 to 2.9. The degree of ethyl substitution represents the average number of hydroxyl groups present on each anhydroglucose unit that have been reacted, which may vary between 0 and 3. The molar substitution represents the average number of hydroxyethyl groups that have reacted with each anhydroglucose unit. One such cellulosic ether is BERMOCOLL E 230FQ, which is an ethyl hydroxyethyl cellulose commercially available from Akzo Nobel. Other suitable cellulosic ethers are also available from Hercules, Inc. of Wilmington, Del. under the name "CULMINAL."

The total concentration of the binders may generally vary depending on the desired properties of the resulting substrate. For instance, high total binder concentrations may provide better physical properties for the coated substrate, but may likewise have an adverse affect on other properties, such as the absorptive capacity or extensibility of the substrate to which it is applied. Conversely, low total binder concentrations may not provide the desired degree of durability. Thus, in most embodiments, the total amount of binder employed in the activated carbon ink (prior to drying) is from about 0.01 wt. % to about 30 wt. %, in some embodiments from about 0.1 wt. % to about 20 wt. %, and in some embodiments, from about 1 wt. % to about 15 wt. %.

Besides the above-mentioned components, a masking agent may also be employed in the activated carbon ink to further alter the aesthetic properties of the substrate. That is, the masking agent may enhance opacity and/or alter the color of the ink. To provide optimum masking effects, the size of the particles is desirably less than the size of any activated carbon particles employed. For example, the masking particles may have a size less than about 100 micrometers, in some embodiments less than about 50 micrometers, and in some embodiments, less than about 25 micrometers. For example, activated carbon particles may sometimes have a particle size of approximately 35 micrometers. In such cases, the size of the masking particles is typically less than 35 micrometers, and preferably much smaller, such as less than about 10 micrometers. Likewise, the particles may be porous. Without intending to be limited by theory, it is believed that porous particles may provide a passage for odorous compounds to better contact the odor adsorbent. For example, the particles may have pores/channels with a mean diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, Vol. 60, 1938, p. 309, with nitrogen as the adsorption gas.

In one particular embodiment, porous carbonate particles (e.g., calcium carbonate) are used to alter the black color normally associated with activated carbon. Such a color change may be more aesthetically pleasing to a user, particularly when the coating is employed on substrates designed for consumer/personal use. Suitable white calcium carbonate particles are commercially available from Omya, Inc. of Proctor, Vermont. Still other suitable particles include, but are not limited to, silicates such as calcium silicate, alumina silicates (e.g., mica powder, clay, etc.), magnesium silicates (e.g., talc), quartzite, calcium silicate fluorite, etc.; alumina; silica; and so forth. The concentration of the particles may generally vary depending on the nature of the particles and the desired extent of odor control and color alteration. For instance, the particles may be present in the ink (prior to drying) in an amount from about 0.01 wt. % to about 30 wt. %, in some embodiments from about 0.1 wt. % to about 20 wt. %, and in some embodiments, from about 1 wt. % to about 15 wt. %.

Other compounds, such as surfactants, electrolytic salts, pH adjusters, etc., may also be included in the activated carbon ink of the present invention. Although not required, such additional components typically constitute less than about 5 wt. %, in some embodiments less than about 2 wt. %, and in some embodiments, from about 0.001 wt. % to about 1 wt. % of the activated carbon ink (prior to drying). For example, as is well known in the art, an electrolytic salt may be employed to control the gelation temperature of a water-soluble binder. Suitable electrolytic salts may include, but are not limited to, alkali halides or sulfates, such as sodium chloride, potassium chloride, etc.; alkaline halides or sulfates, such as calcium chloride, magnesium chloride, etc., and so forth.

To form the activated carbon ink, its components are first typically dissolved or dispersed in a solvent. For example, one or more of the above-mentioned components may be mixed with a solvent, either sequentially or simultaneously, to form an ink formulation that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. The concentration of solvent in the ink formulation is generally high enough to allow easy application, handling, etc. If the amount of solvent is too large, however, the amount of activated carbon deposited on the substrate might be too low to provide the desired odor reduction. Although the actual concentration of solvent employed will generally depend on the type of activated carbon and the substrate on which it is applied, it is nonetheless typically present in an amount from about 40 wt. % to about 99 wt. %, in some embodiments from about 50 wt. % to about 95 wt. %, and in some embodiments, from about 60 wt. % to about 90 wt. % of the ink (prior to drying).

The solids content and/or viscosity of the ink may be varied to achieve the extent of odor reduction desired. For example, the ink may have a solids content of from about 5% to about 90%, in some embodiments from about 10% to about 80%, and in some embodiments, from about 20% to about 70%. By varying the solids content of the ink, the presence of the activated carbon and other components in the activated carbon ink may be controlled. For example, to form an activated carbon ink with a higher level of activated carbon, the ink may be provided with a relatively high solids content so that a greater percentage of activated carbon is incorporated into the activated carbon ink during the application process. Generally, the viscosity is less than about $2 \times 10^6$ centipoise, in some embodiments less than about $2 \times 10^5$ centipoise, in some embodiments less than about $2 \times 10^4$ centipoise, and in some embodiments, less than about $2 \times 10^3$ centipoise, such as measured with a Brookfield viscometer, type DV-I or LV-IV, at 60 rpm and 20° C. If desired, thickeners or other viscosity modifiers may be employed in the ink to increase or decrease viscosity.

The activated carbon ink 12 is applied to the selected substrate component of the pad 10 in a pattern that presents a stark and highly visible contrast against a different color, such as the overall background color of the pad. Thus, instead of being hidden within the pad, the activated carbon ink is used to change the overall appearance of the pad. For example, the activated carbon ink may have a dark color (e.g., black) applied against a contrasting light background. Alternatively, a differently colored foreground may contrast with a dark background provided by the activated carbon ink.

The relative degree of contrast between the odor control ink and the other color may be measured through a gray-level difference value. In a particular embodiment, the contrast may have a gray level value of about 45 on a scale of 0 to about 255, where 0 represents "black" and 255 represents "white." The analysis method may be made with a Quantimet 600 Image Analysis System (Leica, Inc., Cambridge, UK). This system's software (QWIN Version 1.06A) enables a program to be used in the Quantimet User Interactive Programming System (QUIPS) to make the gray-level determinations. A control or "blank" white-level may be set using undeveloped Polaroid photographic film. An 8-bit gray-level scale may then be used (0-255) and the program allowed the light level to be set by using the photographic film as the standard. A region containing the other color (e.g., background or foreground) may then be measured for its gray-level value, followed by the same measurement of the activate carbon ink. The routine may be programmed to automatically calculate the gray-level value of the activated carbon ink. The difference in gray-level value between the activated carbon ink and the other color may be about 45 or greater on a scale of 0-255, where 0 represents "black" and 255 represents "white."

The particular type or style of activated carbon ink pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. The pattern may be targeted for a specific class of consumers. For example, in the case of diapers or training pants, the pattern may be in the form of cartoon characters, animals, and so forth. It should be appreciated that the "pattern" may take on virtually any desired appearance.

Nevertheless, the activated carbon ink usually covers from about 25% to about 95% of the surface area of the substrate, in some embodiments from about 30% to about 90% of the surface area of the substrate, and in some embodiments, from about 30% to about 50% of the surface area of one or more surfaces of the substrate. Not only does such a patterned application have improved aesthetic appeal in comparison to uniformly applied inks, but the present inventors have also discovered that the patterned ink may still achieve good odor reduction. The patterned application of activated carbon ink may also have various other functional benefits, including optimizing flexibility, absorbency, or some other characteristic of the substrate. The patterned application of activated carbon ink may also provide different odor control properties to multiple locations of the substrate. For example, in one embodiment, the substrate is treated with two or more regions of activated carbon ink that may or may not overlap. The regions may be on the same or different surfaces of the substrate. In one embodiment, one region of a substrate is coated with a first activated carbon ink, while another region is coated with a second activated carbon ink. If desired, one region may be configured to reduce one type of odor, while another region may be configured to reduce another type of odor. Alternatively, one region may possess a higher level of an activated carbon ink than another region or substrate to provide different levels of odor reduction.

A variety of techniques may be used for applying the activated ink in the above-described manner. For instance, the ink may be applied using rotogravure or gravure printing, either direct or indirect (offset). Gravure printing encompasses several well-known engraving techniques, such as mechanical engraving, acid-etch engraving, electronic engraving and ceramic laser engraving. Such printing techniques provide excellent control of the composition distribution and transfer rate. Gravure printing may provide, for example, from about 10 to about 1000 deposits per lineal inch of surface, or from about 100 to about 1,000,000 deposits per square inch. Each deposit results from an individual cell on a printing roll, so that the density of the deposits corresponds to the density of the cells. A suitable electronic engraved example for a primary delivery zone is about 200 deposits per lineal inch of surface, or about 40,000 deposits per square inch. By providing such a large number of small deposits, the uniformity of the deposit distribution may be enhanced. Also, because of the large number of small deposits applied to the surface of the substrate, the deposits more readily resolidify on the exposed fiber portions. Suitable gravure printing techniques are also described in U.S. Pat. No. 6,231,719 to Garvey, et al., which is incorporated herein in its entirety by reference thereto for all purposes. Moreover, besides gravure printing, it should be understood that other printing techniques, such as flexographic printing, may also be used to apply the coating.

Still another suitable contact printing technique that may be utilized in the present invention is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the substrate upon which the fluidic channels are to be printed. The ink is painted onto the screen, and transferred by rubbing the screen (which is in contact with the substrate) with a squeegee.

Ink-jet printing techniques may also be employed in the present invention. Ink-jet printing is a non-contact printing technique that involves forcing the ink through a tiny nozzle (or a series of nozzles) to form droplets that are directed toward the substrate. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

In addition to the printing techniques mentioned above, any other suitable application technique may be used in the present invention. For example, other suitable printing techniques may include, but not limited to, such as laser printing, thermal ribbon printing, piston printing, spray printing, flexographic printing, etc. Still other suitable application techniques may include bar, roll, knife, curtain, spray, slot-die, dip-coating, drop-coating, extrusion, stencil application, etc. Such techniques are well known to those skilled in the art.

Regardless of the method of application, the odor control substrate may sometimes be dried at a certain temperature to drive the solvent from the activated carbon ink. For example, the substrate may be heated to a temperature of at least about 50° C., in some embodiments at least about 70° C., and in some embodiments, at least about 80° C. By minimizing the amount of solvent in the activated carbon ink, a larger surface area of activated carbon may be available for contacting odorous compounds, thereby enhancing odor reduction. It should be understood, however, that relatively small amounts of solvent may still be present. For example, the dried ink may contain a solvent in an amount less than about 10% by weight, in some embodiments less than about 5% by weight, and in some embodiments, less than about 1% by weight.

When dried, the relative percentages and solids add-on level of the resulting activated carbon coating may vary to achieve the desired level of odor control. The "solids add-on level" is determined by subtracting the weight of the untreated substrate from the weight of the treated substrate (after drying), dividing this calculated weight by the weight of the untreated substrate, and then multiplying by 100%. One particular benefit of the present invention is that high solids add-on levels and activated carbon levels are achievable without a substantial sacrifice in durability of the coating. In some embodiments, for example, the add-on level of the activated carbon ink is at least about 2%, in some embodiments from about 4% to about 40%, and in some embodiments, from about 6% to about 35%. Further, the coating may contain from about 10 wt. % to about 80 wt. %, in some embodiments from about 20 wt. % from about 70 wt. %, and in some embodiments, from about 40 wt. % to about 60 wt. % of activated carbon. Likewise, the coating may also contain from about 10 wt. % to about 80 wt. %, in some embodiments from about 10 wt. % from about 60 wt. %, and in some embodiments, from about 30 wt. % to about 50 wt. % of binder.

To further improve the aesthetic appeal of the odor control substrate, one or more additional inks may also be employed that contrast with the color of the activated carbon ink (e.g., black). Possible colors that contrast well with a black ink include, for instance, white, yellow, cyan, magenta, red, green, blue, etc. However, any ink may generally be employed so long as some perceivable difference exists between the colors of the inks. To provide the desired color, the colored ink may include a colorant, such as a pigment, dye, etc. The colorant may constitute from about 0.01 to about 20 wt. %, in some embodiments from about 0.1 wt. % to about 10 wt. %, and in some embodiments, from about 0.5 wt. % to about 5 wt. % of the colored ink. For example, the colorant may be an inorganic and/or organic pigment. Some examples of commercially available organic pigments that may be used in the present invention include those that are available from Clariant Corp. of Charlotte, N.C., under the trade designations GRAPHTOL® or CARTAREN®. Other pigments, such as lake compounds (blue lake, red lake, yellow lake, etc.), may also be employed. Inorganic and/or organic dyes may also be utilized as a colorant. Exemplary organic dye classes include triarylmethyl dyes, monoazo dyes, thiazine dyes, oxazine dyes, naphthalimide dyes, azine dyes, cyanine dyes, indigo dyes, coumarin dyes, benzimidazole dyes, paraquinoidal dyes, fluorescein dyes, diazonium salt dyes, azoic diazo dyes, phenylenediamine dyes, diazo dyes, anthraquinone dyes, trisazo dyes, xanthene dyes, proflavine dyes, sulfonaphthalein dyes, phthalocyanine dyes, carotenoid dyes, carminic acid dyes, azure dyes, acridine dyes, and so forth. One particularly suitable class of dyes includes anthraquinone compounds, which may be classified for identification by their Color Index (Cl) number. For instance, some suitable anthraquinones that may be used in the present invention, as classified by their "Cl" number, include Acid Black 48, Acid Blue 25 (D&C Green No. 5), Acid Blue 40, Acid Blue 41, Acid Blue 45, Acid Blue 129, Acid Green 25, Acid Green 27, Acid Green 41, Mordant Red 11 (Alizarin), Mordant Red 13 (Alizarin Blue Black B), Mordant Red 3 (Alizarin Red S), Mordant Violet 5 (Alizarin Violet 3R), Natural Red 4 (Carminic Acid), Disperse Blue 1, Disperse Blue 3, Disperse Blue 14, Natural Red 16 (Purpurin), Natural Red 8, Reactive Blue 2, and so forth.

Besides a colorant, the ink may also include various other components as is well known in the art, such as colorant stabilizers, photoinitiators, binders, solvents, surfactants, humectants, biocides or biostats, electrolytic salts, pH adjusters, etc. For example, various components for use in an ink are described in U.S. Pat. No. 5,681,380 to Nohr, et al. and U.S. Pat. No. 6,542,379 to Nohr, et al., which are incorporated herein in their entirety by reference thereto for all purposes. Such inks typically contain water as a principal solvent, and particularly deionized water in an amount from about 20 wt. % to about 95 wt. % of the ink. Various co-solvents may also be included in the ink formulation. Examples of such co-solvents include a lactam, such as N-methyl pyrrolidone. Other examples of optional co-solvents include N-methylacetamide, N-methylmorpholine-N-oxide, N,N-dimethylacetamide, N-methyl formamide, propyleneglycol-monomethylether, tetramethylene sulfone, and tripropyleneglycolmonomethylether. Still other co-solvents that may be used include propylene glycol and triethanolamine (TEA). If an acetamide-based co-solvent is included in the formulation, it is typically present within a range of from about 1 to about 12 wt. %.

Humectants may also be utilized, such as in an amount between about 0.5 and 20 wt. % of the ink. Examples of such humectants include, but are not limited to, ethylene glycol; diethylene glycol; glycerine; polyethylene glycol 200, 400, and 600; propane 1,3 diol; propylene-glycolmonomethyl ethers, such as Dowanol PM (Gallade Chemical Inc., Santa Ana, Ca;if.); polyhydric alcohols; or combinations thereof. Other additives may also be included to improve ink performance, such as a chelating agent to sequester metal ions that could become involved in chemical reactions over time, a corrosion inhibitor to help protect metal components of the printer or ink delivery system, a biocide or biostat to control unwanted bacterial, fungal, or yeast growth in the ink, a surfactant to adjust the ink surface tension, or a defoamer. If a surfactant is included, it is typically present in an amount of between about 0.1 to about 1.0 wt. %. If a corrosion inhibitor is included, it is typically present in an amount between about 0.1 and about 1.0 wt. %. If a biocide or biostat is included, it is typically present in an amount between about 0.1 and about 0.5 wt. %.

The colored inks may be formed by any known process. For instance, one such process involves mixing all of the components together, heating the mixture to a temperature of from about 40° C. to about 55° C. for a period of from about 2 to about 3 hours, cooling the mixture to room temperature (typically from about 10° C. to about 35° C.), and filtering the mixture to obtain an ink. The viscosity of the resulting ink is typically is no more than about 5 centipoise, and in some embodiments from about 1 to about 2.5 centipoise.

The process for forming a patterned substrate having an activated carbon ink and an additional ink may involve sequentially applying the inks onto one or more surfaces of the substrate. The colored ink may be applied to the same surface as the activated carbon ink so that a readily visible pattern is achieved. Alternatively, the activated carbon ink and colored ink may be applied on opposing surfaces so that the colored ink acts as a contrasting background for the activated carbon ink. The colored ink may generally be applied using any known method, such as those referred to above. The colored ink may be uniformly applied to the substrate surface, or applied in a pattern that covers less than 100% of the area of the surface.

When utilized, the colored and activated carbon inks may be applied in an overlapping or non-overlapping relationship. For instance, in one embodiment, the colored ink may be printed on top of the activated carbon ink in an overlapping relationship. In an alternative embodiment, the activated carbon ink is printed on top of the colored 12. In either case, the top ink generally does not cover the entire surface area of the bottom ink. This is to ensure that the activated carbon ink is able to contact and adsorb odorous compounds, and that a clear pattern is observed. For example, the top ink may cover less than about 90%, in some embodiments less than about 75%, and in some embodiments, less than about 50% of the surface area of the bottom ink.

On the other hand, the colored ink and activated carbon ink may be applied in a non-overlapping relationship. Such a non-overlapping relationship may provide a variety of benefits to the resulting odor control characteristics of the coated substrate. For example, in certain cases, the activated carbon ink might have an adverse affect on the flexibility, absorbency, and/or some other characteristic of the substrate. By minimizing the continuous area to which the activated carbon ink is applied, any such adverse affect is minimized. In addition, a non-overlapping relationship may also provide a clearer definition of the pattern provided by the inks.

The effectiveness of the odor control substrate of the present invention in reducing odor may be measured in a variety of ways. For example, the percent of an odorous compound adsorbed by the odor control substrate may be determined using the headspace gas chromatography test as set forth herein. In some embodiments, for instance, the odor control substrate of the present invention is capable of adsorbing at least about 25%, in some embodiments at least about 45%, and in some embodiments, at least about 65% of a particular odorous compound. The effectiveness of the activated carbon ink in removing odors may also be measured in terms of "Relative Adsorption Efficiency", which is also determined using headspace gas chromatography and measured in terms of milligrams of odor adsorbed per gram of the activated carbon ink. It should be recognized that the surface chemistry of any one type of activated carbon ink may not be suitable to reduce all types of odors, and that low adsorption of one or more odorous compounds may be compensated by good adsorption of other odorous compounds.

Particular illustrative embodiments of an absorbent bed pad 10 are illustrated in FIGS. 2 through 6. It should be appreciated that these embodiments are for illustrative purposes only, and that any variation of patterns of activated carbon ink 12 and contrasting ink 15 applied to any combination of materials of the pad 10 are within the scope and spirit of the invention.

With the embodiment of FIG. 2, the pad includes a cover layer 14 having a pattern of stripes of the activated carbon ink 12 applied thereto. In this particular embodiment, the activated carbon ink 12 is applied only to the cover layer. The pad includes an underlying absorbent structure 16, which may include an absorbent web 17, and an intake or fluid distribution layer 19. It should be appreciated that the absorbent structure 16 may contain any combination of substrates used to intake and absorb fluid that is deposited onto the cover layer 14. The absorbent structure 16 in this case presents a contrasting color to the striped pattern of activated carbon ink 12.

Figure 3:
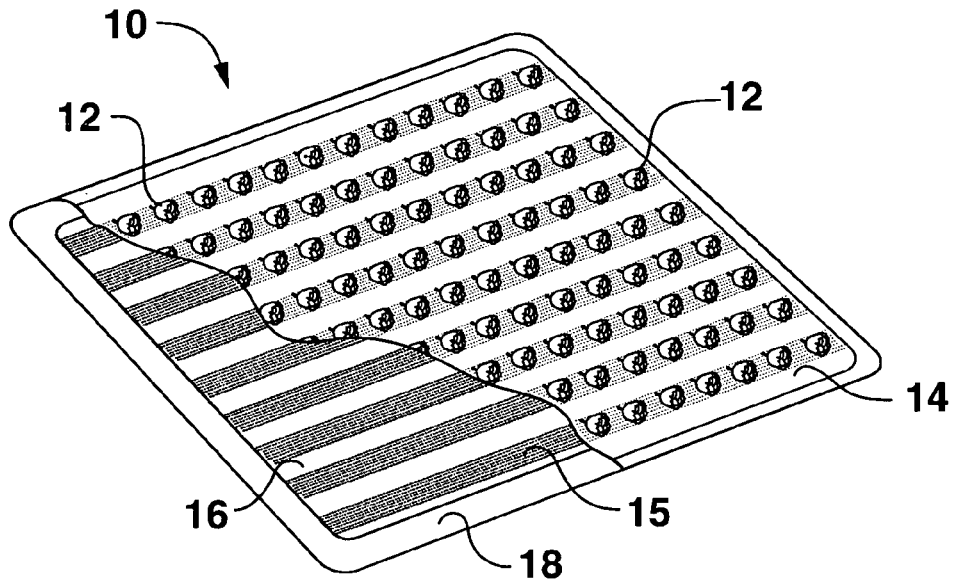
FIG. 3 is a perspective partial cut-away view of a pad embodiment wherein a pattern of activated carbon ink is applied to the cover layer and a pattern of contrasting ink is applied to the underlying absorbent structure.

FIG. 3 depicts an embodiment wherein a pattern of contrasting ink 15 is applied to the underlying absorbent structure 16. A pattern of the activated carbon ink 12 is applied to the cover layer 14 in the form of a floral pattern that is disposed above the stripes of contrasting ink 15 applied to the underlying absorbent 16. With this particular embodiment, the stripes of contrasting ink 15 are visible through the cover layer 14 and present a contrasting background to the floral pattern of activated carbon ink 12.

Figure 4:
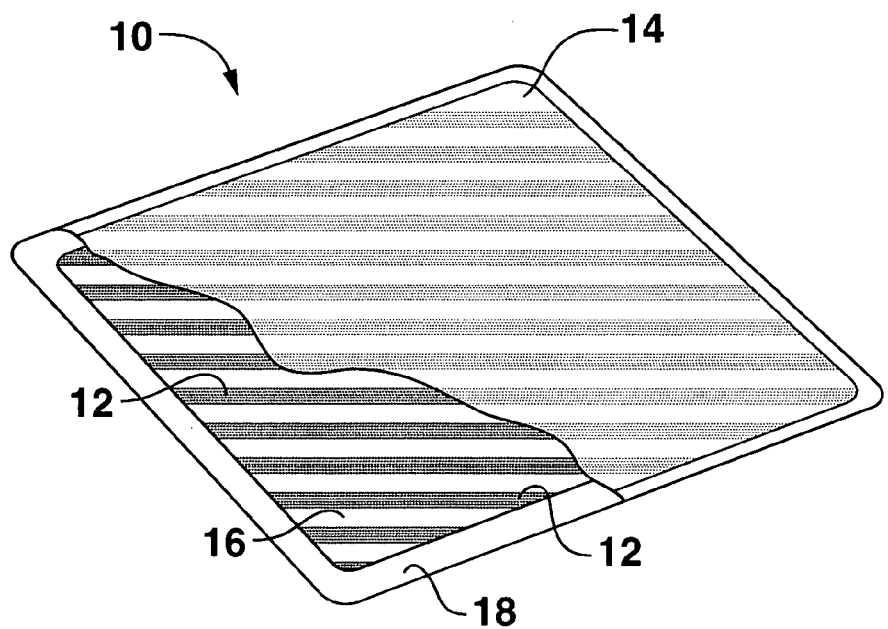
FIG. 4 is a perspective partial cut-away view of a particular embodiment of an absorbent bed pad according to the invention wherein a pattern of activated carbon ink is applied to absorbent structure.

With the embodiment of FIG. 4, the pattern of activated carbon ink 12 is applied in a striped pattern to the underlying absorbent 16. In this particular embodiment, the only component of the pad 10 incorporating the ink 12 is the underlying absorbent 16, and the pattern of stripes is visible through the cover layer 14.

Figure 5:
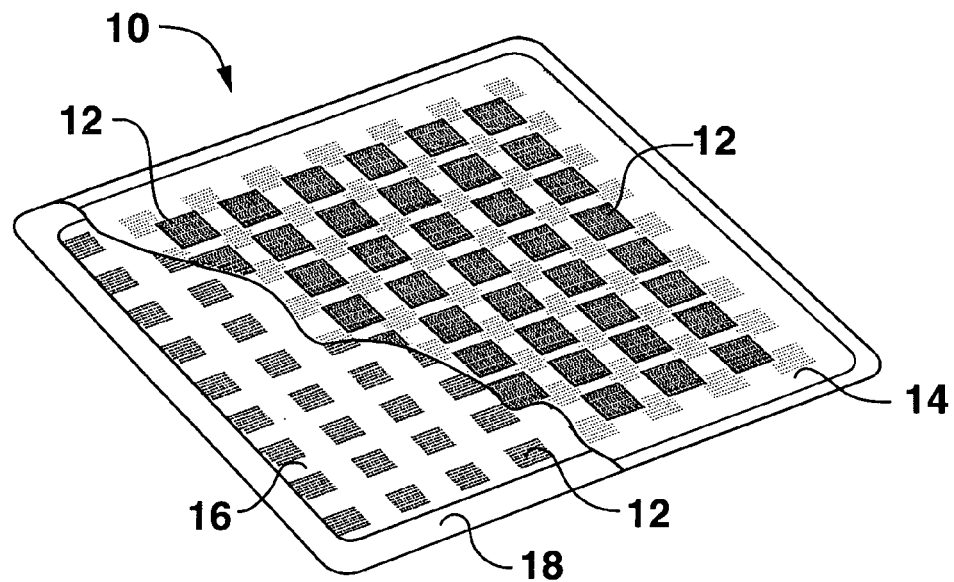
FIG. 5 is a perspective partial cut-away view of an alternate embodiment of an absorbent bed pad according to the invention wherein a pattern of activated carbon ink is applied to the cover layer and underlying absorbent structure of the pad in a partially overlapping configuration.

With the embodiment of FIG. 5, a first pattern of activated carbon ink 12 is applied to the underlying absorbent 16 and is visible through the cover layer 14. A second pattern of activated carbon ink 12 is applied to the cover layer 14 and partially overlaps the underlying pattern applied to the absorbent structure 16. Thus, the underlying activated carbon 12 and background color of the absorbent structure 16 presents a contrast to the pattern of activated carbon 12 applied to the cover layer 14. It should be appreciated that the different applications of the activated carbon ink 12 may be completely overlapping, partially overlapping, or non-overlapping.

Figure 6:
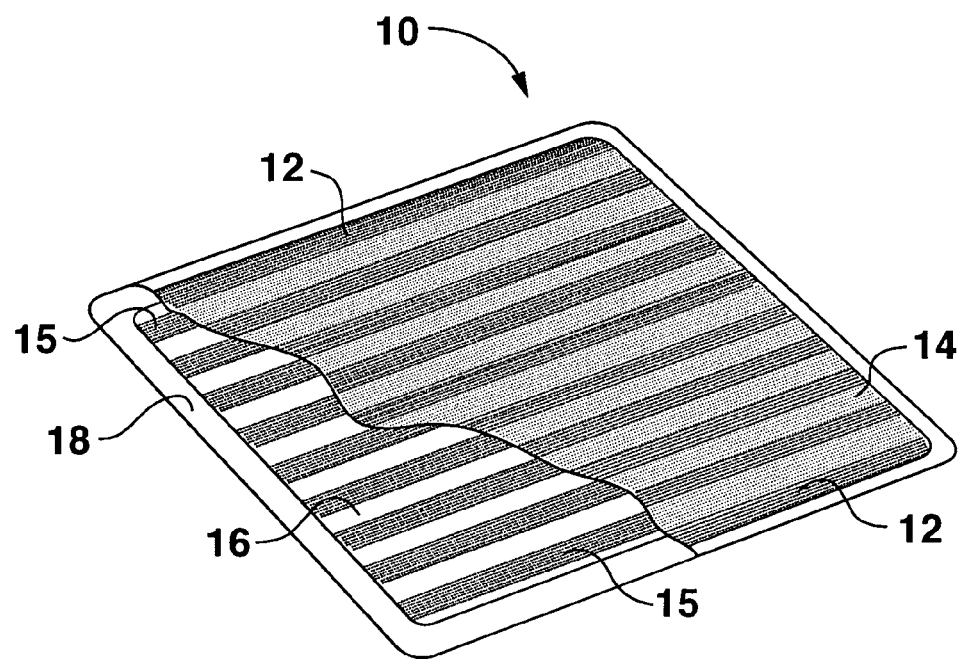
FIG. 6 is a perspective partial cut-away view of a particular embodiment of an absorbent bed pad according to the invention wherein a pattern of activated carbon ink is applied to the cover layer of the pad and an offset pattern of contrasting ink is applied to the underlying absorbent structure.

In the embodiment of FIG. 6, a striped pattern of contrasting ink 15 is applied to the underlying absorbent structure 16 and is visible through the cover layer 14. An offset pattern of activated carbon ink 12 is applied to the cover layer 14 so as not to overlap the pattern of contrasting ink 15. It should be appreciated that any number of patterns and configurations may be used to accomplish this result.

The present invention may be better understood with reference to the following examples.

Test Methods

Quantitative odor adsorption was determined in the Examples using a test known as "Headspace Gas Chromatography." Headspace gas chromatography testing was conducted on an Agilent Technologies 5890, Series II gas chromatograph with an Agilent Technology 7694 headspace.sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the odorous compound that had a length of 30 meters and an internal diameter of 0.25 millimeters. Such a column is available from J&W Scientific, Inc. of Folsom, Calif.

The operating parameters used for the headspace gas chromatography are shown below in Table 1:

TABLE 1

| Operating Parameters for the Headspace Gas Chromatography Device. Headspace Parameters | | |
|---|---|---|
| Zone Temps, °C. | Oven | 37 |
|  | Loop | 85 |
|  | TR. Line | 90 |
| Event Time, minutes | GC Cycle time | 10.0 |
|  | Vial eq. Time | 10.0 |
|  | Pressuriz. Time | 0.20 |
|  | Loop fill time | 0.20 |
|  | Loop eq. Time | 0.15 |
|  | Inject time | 0.30 |
| Vial Parameters | First vial | 1 |
|  | Last vial | 1 |
|  | Shake | [off] |

The test procedure involved placing 0.005 to 0.1 grams of a sample in a 20 cubic centimeter (cc) headspace vial. Using a syringe, an aliquot of an odorous compound was also placed in the vial. Specifically, testing was done with 2.0 micrograms of ethyl mercaptan (2.4 microliters) and 1.8 micrograms (2 microliters) of dimethyldisulfide. The samples were tested in triplicate. After ten minutes, a hollow needle was inserted through the septum and into the vial. A 1-cubic centimeter sample of the headspace (air inside the vial) was then injected into the gas chromatograph. Initially, a control vial with only the aliquot of odorous compound was tested to define 0% odorous compound adsorption. To calculate the amount of headspace odorous compound removed by the sample, the peak area for the odorous compound from the vial with the sample was compared to the peak area from the odorous compound control vial.

EXAMPLE 1

The ability to apply activated carbon ink to a substrate for use in an absorbent bed pad was demonstrated. The activated carbon ink was made by MeadWestvaco Corp. under the name "Nuchar PMA", and contained 15 wt. % activated carbon, 12 wt. % styrene-acrylic copolymer binder, and 73 wt. % water. The ink was coated onto polyethylene film, cellulose tissue, and SMS fabric using a standard off-set gravure printing system to uniformly print the activated carbon ink onto one side of the respective substrates. The coating add-on level was between 3-10 gsm. The coated substrates were then incorporated into a commercially obtained absorbent bed pad.

Table 2 shows the activated carbon ink add-on levels of an absorbent web of cellulose tissue substituted into the bed pads.

TABLE 2

| Activated Carbon Ink Coating of Cellulose Tissue Samples | | | | |
|---|---|---|---|---|
| Sample | Initial Weight (g) | Net Weight (g) | Add-On Level (%) based on solution concentration and wet pick-up | Add-On Level (%) (based on dry weight) |
| Control | — | — | — |  |
| 1 | 0.87 g | 2.80 g | 33% | 30% |
| 2 | 0.87 g | 3.25 g | 41% | 39% |

The tissue samples were then tested for their ability to remove ethyl mercaptan (EtSH), ammonia (NH3), and triethylamine (TEA) and dimethylsulfide odorous compounds using the headspace gas chromatography test described above. The results are set forth below in Table 3.

TABLE 3

Odor Reduction Analysis of Carbon Ink Coated Tissue

| Sample | EtSH (2.4 uL) % remv'd | EtSH (2.4 uL) mg odor/g sample | NH3 (6 uL) % remv'd | NH3 (6 uL) mg odor/g sample | TEA (5 uL) % remv'd | TEA (5 uL) mg odor/g sample |
|---|---|---|---|---|---|---|
| Control tissue | 22.88 | 7.25 | 0.14 | 0.03 | 50.3 | 15.38 |
| 1 | 54.66 | 15.83 | 35.88 | 6.22 | 95.96 | 31.74 |
| 2 | — | — | 35.88 | 6.21 | 79.70 | 25.14 |

Thus, from the GC Headspace analysis the activated carbon coating has excellent absorption of ammonia, sulfur-based and amine-based odors. These odors are the major components of malodors such as urine, feces (human and animal), perspiration, pet odor, mold/mildew, spoiled foods such as meats and vegetables. Pads according to the invention incorporating the activated carbon ink have the utility to absorb and reduce these common odors. The pads could be used for additional applications such as pet bed pads, diaper changing pads, food preparation or storage pads, garbage bag liners or inserts, diaper pail liners or inserts.

Urine Odor Control Assessment of Model Pads

A series of human urine odor ranking panel assessments were conducted on pads to confirm real world odor situations and determine the efficacy and efficiency of the pads. Feminine incontinence pads (POISE® pad from Kimberly-Clark Corp.) were used as models for bed pads since they are constructed in a similar manner and have similar components. The smaller size of the POISE® pads allowed the sample pads to fit in a Mason jar for assessment and ranking by trained odor panel personnel. The POISE® pads are constructed with a fluid permeable, nonwoven body side liner, a surge layer disposed below the body side liner, a tissue wrapped pledget of cellulosic fluff and Super Absorbent Particles (SAP) below the surge layer, and a fluid impermeable PE film as the garment side liner. The activated carbon ink can easily be applied to any of the various components of the pad.

A urine odor evaluation panel study (ORP) was performed on regular POISE® Pads (Adult Care) having strips of activated carbon ink coated tissue, nonwoven material, or polyethylene film placed at various locations inside the pads. The pads were then insulted with pooled female urine (60 ml) and incubated for 24 hours in Mason jars (1 quart) with lids. Twelve women panelists ranked the pads in order of most to least urine odor intensity. The study included POISE® and Serenity Night & Day pads as controls. The pad with the least odor was a design in which the existing tissue wrap was replaced with the carbon ink coated tissue.

Table 4 shows the ranking of overall urine odor intensity for all of the codes placed in the study.

TABLE 4

Urine Odor Ranking ORP Study

| SAMPLE | URINE ODOR Ranking Overall urine intensity |
|---|---|
| POISE ® Control | 30.6 (most odor) |
| Serenity Night & Day | 28.8 |
| Carbon H1500 (5 mg of carbon powder) | 17.6 |
| Carbon coated polyethylene film (34 mg carbon per pad) | 9.7 |
| Carbon coated tissue wrap (TW2, 21 mg carbon per pad) | 8.0 |
| Carbon coated tissue wrap (TW1, 31 mg carbon per pad) | 5.3 (least odor) |

The above results (see Table 4) show that the carbon ink containing pads have significantly less urine odor than the controls. Of the carbon ink coated substrates, the carbon ink treated tissue wrap samples had the least urine odor. The difference between Tissue Wrap 1 (TW1) and Tissue Wrap 2 (TW2) was that TW1 had 10mg more carbon than TW2.

A surprising result of the study was that the polyethylene film having one side coated with the carbon ink and inserted at the bottom of the pad behind all of the absorbent components still had significant odor removing ability.

It should also be noted that, the pad with activated carbon powder did not perform as well as the carbon ink coated substrates. This is thought to be due in part to the carbon ink providing a high surface area coated substrate for maximum odor absorption. The powder has a smaller surface area per pad and therefore does not absorb as much odor. This pad did not deliver a significant urine odor reduction.

An additional study was carried out with hand-coated substrates which were incorporated into the POISE® pads. This study was to explore the effect of using different designs to cover the pledget (SAP/fluff) and to determine the effect on the odor reduction. The following describes the methods used:

Full replacement of tissue wrap with the carbon coated tissue.

Carbon coated tissue covering the length of the pledget with the side of the pledget left open (uncovered).

Covering the ends of the pledget only with carbon coated wetlaid fabric The urine odor was assessed by the ORP panel. The results are shown in the Table 5 below.

TABLE 2

Urine Odor Ranking Panel Study

| SAMPLE | Rank Overall Urine Odor Intensity after 24 hours |
|---|---|
| Serenity Night & Day | 31.8 (Most Odor) |
| POISE ® Control | 16.6 |
| Tissue wrap (11 mg carbon) | 16.4 |
| Open side Wetlaid (43 mg carbon) At ends of pledget | 9.3 |
| Tissue wrap (23 mg carbon) | 8.6 (Least odor) |

The above results show that by simply replacing the tissue wrap with carbon coated tissue wrap significantly reduced the urine odor in the pad. Partially covering the pledget did reduce the urine odor but not as well as the full tissue wrap.

Gasoline, Garlic and Cigarette Odor Reduction Evaluation of Pads

To further explore the utility of pads according to the invention, an odor evaluation was conducted to assess the application of the pads to remove other common odors. The odor ranking panel was conducted by placing 3"×3" squares of tissue coated with carbon ink into Mason jars (one quart) that already contained samples of the following common odorous materials:
0.25 ml of regular gasoline.
100 mg of freshly sliced garlic.
Cigarette end (previously smoked and extinguished).
An identical series of control jars were prepared into which was placed uncoated tissue samples (control). The odor panelists were then asked to assess and rank the Mason jars by odor intensity. The mason jars were wrapped with aluminum foil on the outside to ensure a blind study. The following table shows the results of the odor ranking panel study.

TABLE 6

Odor Ranking Study of pads with Cigarette, Garlic and Gasoline Odors

| Odors (major chemical type) | Control Tissue Odor Ranking (4 panelists) | Carbon Ink Coated Tissue Odor Ranking (4 panelists) |
| --- | --- | --- |
| Gasoline (hydrocarbon odor) | 40 | 4 (ranked least odor) |
| Garlic (sulfur-based odor) | 40 | 4 (ranked least odor) |
| Cigarette (acid + aldehyde-based odor) | 40 | 4 (ranked least odor) |

These results illustrate a broad utility and efficiency of the activated carbon coated substrate to absorb and reduce commonly found odors.

Aesthetically Pleasing Multicolored Printed with Activated Carbon

Cellulose tissue sheets (tissue wrap) were printed with activated carbon ink using a hand-held rubber roller. Various stencils were purchased from a craft store and used as illustrations for printing patterns having different print areas. Multiple color inks (yellow, cyan and magenta) were also printed via a rubber roll. In a first experiment, activated carbon ink (MeadWestvaco, Nuchar PMA) was applied first to the tissue wrap using the stencil followed by a color ink, e.g. yellow, on the opposite side of the tissue wrap. Due to the opacity of the carbon ink, the color did not penetrate the black ink. The yellow color presented a stark contrast to the stencil pattern of activated carbon ink.

In a separate experiment, two samples of tissue wrap were printed on the same side with the yellow color ink and the carbon ink (black). The first sample was printed with the yellow ink as a background and the carbon ink stenciled over the yellow ink. The other sample was printed with the carbon ink as the background and the yellow ink applied over the carbon ink in a stenciled pattern. A stark contrast between the colors was presented in both samples.

Additional experiments were conducted with multiple color inks in various combinations with the activated carbon ink (black), including coating the tissue wrap on one side with the carbon ink and applying different color ink on the opposite side in a stenciled pattern. A highly visible and aesthetically pleasing contrasting pattern was presented in all samples.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent pad configured to absorb fluids and control odors, said pad comprising:
    a liquid-permeable cover layer, a liquid-impermeable back sheet, and an absorbent structure disposed between said cover layer and said back sheet;
    at least one of said cover layer, said back sheet, or said absorbent structure incorporating a dried application of a liquid activated carbon ink having activated carbon, a binder, and a solvent, said dried application of said ink having a solids add-on level of at least about 2%, said activated carbon ink applied in a first pattern over between about 25% to about 95% of a total upper surface area of said pad, said dried activated carbon ink presenting a visually contrasting color against a background color of said pad;
    a dried application of an additional ink applied in a second pattern on at least one of said cover layer, said back sheet, or said absorbent structure so as to present a visually distinguishing pattern against the background color of said pad when viewed from said cover layer, said additional ink also presenting a color that is visually distinguishable from the color of said activated carbon ink;
    wherein said first pattern of activated carbon ink and said second pattern of additional ink are visually distinguishable from each other, and are both visually distinguishable against the background color of said pad, and
    wherein said additional ink comprises activated carbon in a formulation so as to be configured to reduce one type of odor while said activated carbon ink is configured to reduce another type of odor.

2. The pad as in claim 1, wherein said activated carbon is present in an amount from about 1 wt. % to about 50 wt. % of said liquid activated carbon ink.

3. The pad as in claim 1, wherein said binder is present in an amount from about 0.01 wt. % to about 30 wt. % of said liquid activated carbon ink.

4. The pad as in claim 1, wherein said solvent is present in an amount from about 40 wt. % to about 99 wt. % of said liquid activated carbon ink.

5. The pad as in claim 1, wherein said pattern of dried activated carbon ink covers from about 30% to about 90% of said surface area.

6. The pad as in claim 1, wherein the contrast between the color of said dried activated carbon ink and said background color has a minimum gray scale value of at least about 45 on a scale of 0-255.

7. The pad as in claim 1, wherein said liquid activated carbon ink and said additional ink are applied in an at least partially overlapping relationship.

8. The pad as in claim 1, wherein said liquid activated carbon ink and said additional ink are applied in a non-overlapping relationship.

9. The pad as in claim 1, wherein said liquid activated carbon ink is applied to only one of said cover layer, said back sheet, or said absorbent structure.

10. The pad as in claim 1, wherein said liquid activated carbon ink is applied to at least two of said cover layer, said back sheet, or said absorbent structure.

11. The pad as in claim 10, wherein said liquid activated carbon ink is applied in overlapping regions of said cover layer, said back sheet, or said absorbent structure.

12. The pad as in claim 1, wherein said liquid activated carbon ink is applied at an add-on level of between about 3 to about 10 gsm.

13. The pad as in claim 1, wherein said liquid activated carbon ink is applied at an add-on level of between about 3 to about 6 gsm.

14. The pad as in claim 1, wherein said pad is a bed pad configured for placement under a patient to absorb bodily exudates and fluids.

15. The pad as in claim 1, wherein said liquid activated carbon ink is present in an amount sufficient for decreasing at least by half odor intensity from any one of the group of pet odors, cigarette odor, smoke, foods, and animal odors.

16. The pad as in claim 1, wherein said liquid activated carbon ink and said additional ink are applied to different ones of said cover layer, said back sheet, or said absorbent structure.

17. The pad as in claim 1, wherein said liquid activated carbon ink and said additional ink are applied to the same one of said cover layer, said back sheet, or said absorbent structure.

18. The pad as in claim 17, wherein said liquid activated carbon ink is applied in said first pattern directly onto said second pattern of additional ink.

19. The pad as in claim 17, wherein said additional ink is applied in said second pattern directly onto said first pattern of dried application of liquid activated carbon ink.

* * * * *

UNITED STATES PATENT AND TRADEMARK OFFICE
CERTIFICATE OF CORRECTION

PATENT NO.       : 7,655,829 B2                                    Page 1 of 1
APPLICATION NO.  : 11/194102
DATED            : February 2, 2010
INVENTOR(S)      : MacDonald et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 552 days.

Signed and Sealed this

Twenty-third Day of November, 2010

David J. Kappos
*Director of the United States Patent and Trademark Office*